United States Patent
Foschini et al.

(10) Patent No.: US 9,439,908 B2
(45) Date of Patent: Sep. 13, 2016

(54) CROSS-LINKING COMPOSITION DELIVERED BY IONTOPHORESIS, USEFUL FOR THE TREATMENT OF KERATOCONUS

(71) Applicant: SOOFT ITALIA SPA, Montegiorgio (FM) (IT)

(72) Inventors: Fulvio Foschini, Rome (IT); Marcello Stagni, Catania (IT); Giulio Luciani, Bagno a Ripoli (IT); Pierre Roy, Paris (FR)

(73) Assignee: SOOFT ITALIA SPA, Montegiorgio (FM) (IT)

( * ) Notice: Subject to any disclaimer, the term of this patent is extended or adjusted under 35 U.S.C. 154(b) by 76 days.

(21) Appl. No.: 14/353,872

(22) PCT Filed: Oct. 24, 2012

(86) PCT No.: PCT/IT2012/000324
§ 371 (c)(1),
(2) Date: Apr. 24, 2014

(87) PCT Pub. No.: WO2013/061350
PCT Pub. Date: May 2, 2013

(65) Prior Publication Data
US 2014/0303173 A1    Oct. 9, 2014

(30) Foreign Application Priority Data
Oct. 25, 2011  (IT) ............. RM2011A0560

(51) Int. Cl.
*A61K 31/525*   (2006.01)
*A61K 9/00*   (2006.01)

(52) U.S. Cl.
CPC ........... *A61K 31/525* (2013.01); *A61K 9/0009* (2013.01); *A61K 9/0048* (2013.01)

(58) Field of Classification Search
CPC .................................................... A61K 31/525
See application file for complete search history.

(56) References Cited

U.S. PATENT DOCUMENTS

2003/0023228 A1*  1/2003  Parkinson et al. ............ 604/521

FOREIGN PATENT DOCUMENTS

| WO | 2009/001396 A1 | 12/2008 |
| WO | 2010/023705 A1 | 3/2010 |
| WO | 2011/130356 A2 | 10/2011 |

OTHER PUBLICATIONS

George Waring: "Old technique, new delivery", Ophthalmology Times Conference Brief, Oct. 22, 2011, XP55027064, Internet Retrieved from the Internet: URL:http://ophthalmologytimes.modernmedici ne.com/phthalmologytimes/ModernMedicine+Now/Old-technique-new-delivery/ArticleStandard/Article/detail/745363 [retrieved on May 14, 2012] cited in the application the whole document.
Edoardo Stagni: "Riboflavin Ophthalmic Medical Device", Internet Article, Feb. 2, 2007, pp. 1-24, XP002502745, Retrieved from the Internet: URL:http://www.assocheratocono.org/public2/documenti/Riboflavin.pdf [retrieved on Nov. 6, 2008] the whole document.
International Search Report, dated Apr. 5, 2013, from corresponding PCT application.

* cited by examiner

Primary Examiner — Zohreh Fay
(74) Attorney, Agent, or Firm — Young & Thompson

(57) ABSTRACT

An improved formulation of an ophthalmic composition contains riboflavin, as cross-linking agent of corneal collagen, administered by corneal iontophoresis, able to guarantee an increased capacity of permeation of riboflavin of the corneal stroma and therefore greater therapeutic efficacy in the treatment of keratoconus.

11 Claims, 1 Drawing Sheet

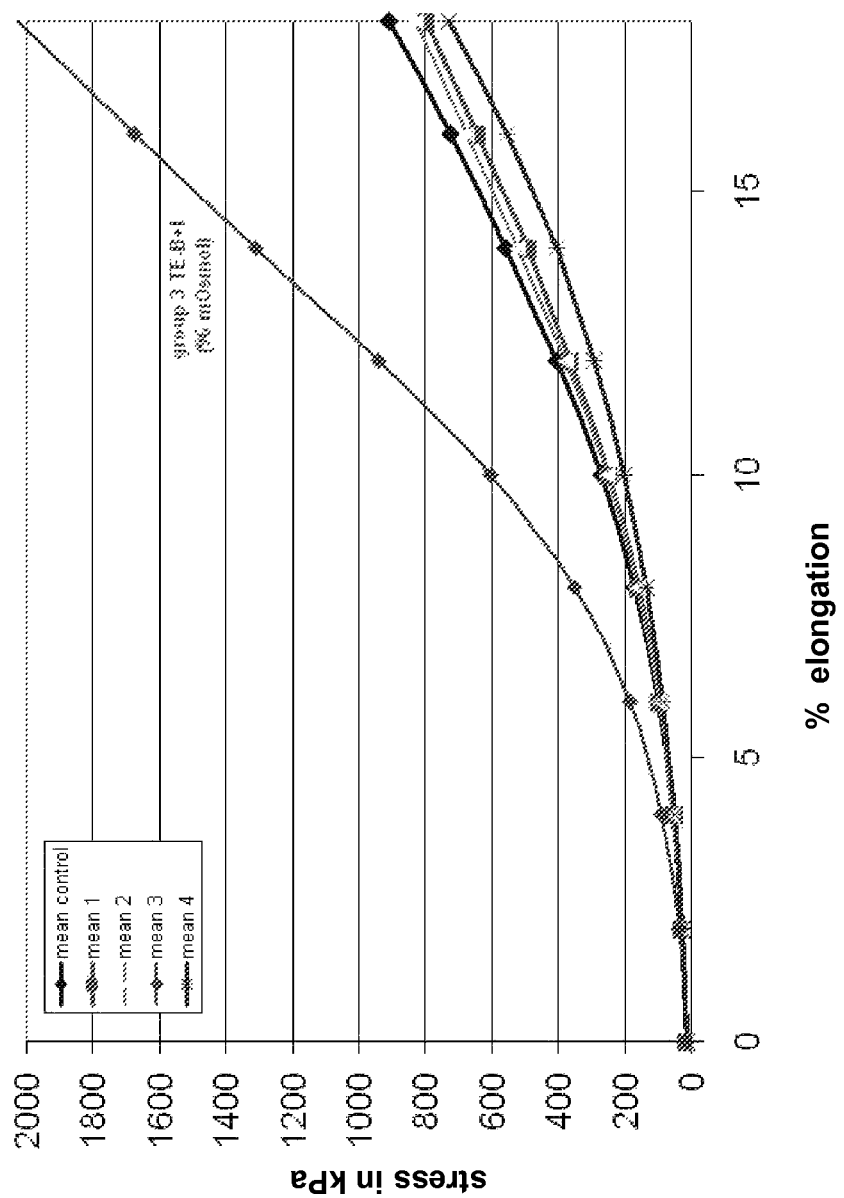

CROSS-LINKING COMPOSITION DELIVERED BY IONTOPHORESIS, USEFUL FOR THE TREATMENT OF KERATOCONUS

BACKGROUND OF THE INVENTION

1. Field of the Invention

The present invention relates to the medical pharmaceutical field and, more specifically, the field of preparations for topical ophthalmic use to be administered by means of iontophoresis to perform the cross-linking (CXL) of corneal collagen useful in the treatment of keratoconus, in particular an improved formulation of an ophthalmic composition containing riboflavin.

2. Description of the Related Art

The collagen cross-linking induced by riboflavin and UV-A, is a practice widely used in ophthalmology, it consists in the photopolymerization of stromal collagen fibrils with the purpose of increasing its rigidity and resistance to progressive keratoectasia of keratoconus through the combined action of a photosensitizer and light-absorbing substance, the riboflavin precisely, by irradiation with ultraviolet light from UV-A type illuminator.

The purpose of the present invention is to provide an ophthalmic solution of riboflavin, as improved cross-linking agent, to be administered by means of iontophoresis in the practice of the treatment of keratoconus, or of other ectatic corneal diseases, having improved permeation and penetration characteristics in the corneal stroma, considerably reducing the time required for the treatment and improving performance and therapeutic outcomes.

Similarly to the brain, eye is protected by biological barriers (the blood-eye barrier, the blood-vitreous barrier) that make difficult the administration of medicaments at sufficient concentration, especially in the posterior segments of the eye. Through the systemic via (by oral or intravenous administration) only a small fraction of the initial amount of drug may be delivered to interior eye tissues, so it is insufficient.

As topical application of eye drops fails to treat the posterior segment of the eye, the penetration is very limited (normally less than 5%), techniques for local administration of medicaments to the eye have been developed and are subjected to continuous and intense study to improve its efficiency. The direct injection around the eyeball (peribulbar, retrobulbar), or within the eyeball (intraocular), is very traumatic. The photodynamic therapy, consisting in the injection of the medicament and in its systemic activation in situ using a laser at specific wavelengths, takes advantage of the transparency of the cornea but it has the disadvantage that the patient must remain in the dark, the medicament must be modified by the addition of a photosensitizing agent preventing the active principle from acting before it is activated by light, also requires the use of special and expensive instrumentation in order to be carried out. Numerous devices designed to convey medicaments in a continuous or programmed manner by the use of medicament tanks placed on the surface of the eye have been also developed, said devices are therefore non-invasive, or in the form of lenses or rings in the conjunctival sac. However, the passage of substance to the posterior segment of the eye is limited, therefore the use of these devices is limited to the treatment of pathologies of the anterior ocular segment, for example, for the treatment of conjunctivitis. Intraocular implants for the programmed release of medicaments surgically positioned in the vitreous humor have the serious risk to damage the retina by contact, since incisions of relatively large size (5 mm) are required to place the implant. Another significant drawback concerns the possible need to replace the implant, or to intervene to interrupt or modify the treatment as a function of how the disease responds to treatment.

In order to improve the corneal absorption of the riboflavin, commonly used as a photosensitizing and curing agent in the process of corneal cross-linking, without having to resort to removal of corneal epithelium, and to obtain in such a way a non-invasive corneal cross-linking, eliminating or reducing anesthesia and resulting in a more rapid healing, patent application WO 2010/023705 has suggested the use of absorption enhancers, including EDTA associated with tromethamine and/or salts of EDTA associated with tromethamine, to form an ophthalmic composition administered in the form of eye drops to be instilled on the corneal surface.

Another possible solution is to use ocular iontophoresis.

This is another technique for administrating active ingredients with therapeutic action which allows to reduce most of the disadvantages of other techniques for ocular administration. In fact it makes possible, in a non-invasive manner, to reach concentrations and residence times in the eye, and hence transfer efficiencies, equal to or greater than those obtained with other techniques of the state of the art.

The principle underlying the iontophoresis involves the application of an electric field to an electrolyte composition containing at least one medicament in order to transport the medicament or medicaments in the body through biological membranes. The technique has long been clinically used in dermatology, in the treatment of osteoarticular disorders, but more recently has proved being particularly suitable for transferring active ingredients and drugs into the eye.

However, because the eye is extremely different from most of the organs of the other body districts, ocular iontophoresis must submit technical specificities different from those of other types of iontophoresis (intensity and current density, duration and control of the applied electric field, physical aspects of the chemical substances to be administered, electrochemical phenomena that occur in the solution during administration).

In particular, international patent application WO 2011/130356 claims a method to activate the cross-linking in at least one component of the eye comprising the transport of the electrically charged cross-linking agent to the ocular component pushing it in depth using the iontophoretic process and the activation of the cross-linking agent conveying an initiation element to the eyepiece element, wherein the eyepiece element is the cornea, the limbus, the sclera and the retina. According to the teachings of said patent application the cross-linking agent, such as riboflavin, can be combined in various concentrations with other agents such as EDTA, benzalkonium chloride, or an alcohol to promote the further transfer across the corneal surface. However, the description does not define amounts or concentrations of the various components of the cross-linking agent.

There is an ongoing debate in the ophthalmic field about the best way to transfer to the cornea riboflavin to perform cross-linking of corneal collagen, the results of clinical studies indicate that the iontophoretic application of riboflavin should decrease processing time and eliminate the recourse to corneal epithelium removal before treatment. The internet publication of the document of George Waring: "Old technique, new delivery", Ophthalmology Times Conference Brief, Oct. 22, 2011, URL: http://ophthalmology-times.modernmedicine.com/ophthalmologytimes/Modern-Medicine+Now/Old-technique-new-delivery/Article Standard/Article/detail/745363, discloses that the iontophoretic treatment accelerating the riboflavin transfer eliminates the need of corneal epithelium removal.

The applicants of the present patent application have already described in patent application WO 2012/095877, filed on 12 Jan. 2011, the use of iontophoresis to deliver ophthalmic compositions, preferably containing riboflavin or other agents promoting cross-linking, designed to permeate the corneal stroma in the practice of corneal cross-linking of collagen in the treatment of keratoconus and other ectatic conditions of the eye. Due to the increased transfer efficiency promoted by the electric current, the administration time is significantly reduced, and the procedure is much more comfortable for the patient.

The ophthalmic compositions described in the aforementioned patent application are specifically designed to increase their transfer ability within and through the eye, by means of iontophoresis. In particular, the compositions described are based on riboflavin, between 0.1 and 1%, or other cross-linking agents that at the same time are also characterized by buffering properties, such as sodium phosphate. In such a way the described compositions improve permeation and penetration in the corneal stroma without having to proceed to the removal of the corneal epithelium in the treatment of keratoconus, or of other corneal ectatic diseases, by means of cross-linking corneal. According to said patent application, the ophthalmic solutions to be transferred by means of iontophoresis must have a initial value of pH in the range between 5 and 8 in order to act as a buffering agent and reach a final value not greater than 9. Furthermore, the presence of dextran guarantees a good adhesiveness to the ocular surface, ensures a better contact and thus a better permeation of the corneal stroma by the riboflavin solution.

However, despite the considerable improvement provided by the ocular iontophoretic administration, always remains particularly felt the need to improve the effectiveness of the ocular transfer by means of iontophoresis in order to further reduce the risks of causing burns, irritations and general toxicity phenomena in the tissues that in the long may limit the application of ocular iontophoresis. It would be desirable to further reduce the time to achieve iontophoresis to reduce the potential risks during the execution of the process and improve the comfort of the patient.

The parameters on which the expert is able to intervene in order to improve the effectiveness and the success of the ocular iontophoretic procedure are many and of different nature, in fact, they relate to: the area of application of the electric field, sclera rather than cornea, this latter particularly delicate; minimizing the density of the electric field, the application area and the electrode area; controlling the intensity of the electric field applied so as to achieve a good reproducibility; limiting the application; and finally, the characteristics of the solution to be transferred.

SUMMARY OF THE INVENTION

The object of the present invention is therefore to provide new formulations, useful for the treatment of keratoconus, based on riboflavin, suitable to be administered by iontophoresis, characterized by a better transepithelial penetration in the corneal stroma compared to the formulations of the state of the art.

The improved capacity of permeation and penetration into the corneal stroma, without having to proceed to the removal of the corneal epithelium in the practice of the treatment of keratoconus, or of other corneal ectatic diseases, by means of corneal cross-linking, was evaluated as a function of increase in corneal rigidity of the eye treated with the formulations object of the present invention compared to those of the prior art.

Thus, an object of the invention is to provide a formulation of a specific product based on riboflavin, suitable for the permeation of the cornea, in view of CXL treatment, which have to be transferred to the cornea by means of iontophoresis and subsequently irradiated by UV light. More particularly, it is an object of the present invention to provide solutions particularly suitable to be administered by iontophoresis, having values of pH and osmolarity able to ensure an optimal osmotic flow and in the appropriate direction with respect to the transfer of the riboflavin solution, which must operate the cross-linking of the collagen fibers of the corneal stroma in response to irradiation with UV.

Because iontophoresis substantially is the promotion of a movement of a charged substance through a biological membrane by the application of an electric field, osmolarity and pH are very important and determinant physical parameters of transfer effectiveness by means of iontophoresis of a solution. When the electric field is applied across a membrane and yields the movement of solvent bearing neutral or ionic species an electrosmotic flow is established which is proportional to the concentration of ionic and neutral species of the active ingredient to be transferred. The direction of the electrosmotic flow takes place in the direction of the counterions of the charge of the membrane. At physiological pH value (pH=7.4), the skin, as most of the biological membranes, including cornea and sclera, is negatively charged. Therefore, the electrosmotic current strengthens the anode transfer (+) of the drug positively charged, while the cathode transfer (−) of the drug negatively charged is delayed. At low pH values, the charge of the biological surface shifts to the positive and the osmotic flow is reversed. This explains the importance of the pH value of the solution to be administered by iontophoresis, which in addition to protect from damage to the conjunctiva and the cornea (the eye can tolerate a pH range rather wide and the pH of the ophthalmic solutions can vary from 4.5 to 11.5, however the range of pH values useful for preventing corneal damage is from 6.5 to 8.5), also maintains the relative contribution of the osmotic flow at an appropriate level and direction. In addition, if the duration of the applied current is kept short, the number of ionic species in the solution is stable.

In a preferred embodiment of the invention formulations based on riboflavin phosphate have been identified showing optimal parameters relatively to the measurements of pH and osmolarity. In particular, the formulations according to the present invention have a pH value between 6.5 and 8, preferably the pH value of the formulations is between 6.9 and 7.2, even more preferably the pH value is 7,0, while the value of osmolarity of the formulations is between 90 mOsm/l and 300 mOsm/l, preferably 96 mos/l.

BRIEF DESCRIPTION OF THE DRAWING FIGURES

FIG. 1 shows the obtained experimental results in a stress vs. tension curve of the eye treated with the formulations according to the present invention.

According to a particular embodiment of the invention the formulations are dextran free. In fact, surprisingly, recent studies carried out by the applicants of the present patent application have shown that permeation and penetration characteristics in the corneal stroma of riboflavin, without having to proceed to the removal of the corneal epithelium in the practice of the treatment of keratoconus or of other ectatic corneal diseases, evaluated a posteriori as a function of the corneal rigidity following CXL treatment, are significantly improved by using solutions that, in contrast to what had been assumed previously, contain neither dextran nor sodium chloride.

Further advantages and features of the invention will be evident from the detailed description of the invention with reference also to the enclosed FIGURE purely by way of example, and not limitation.

DETAILED DESCRIPTION OF THE INVENTION

FIG. 1 shows the obtained experimental results in a stress vs. tension curve of the eye treated with the formulations according to the present invention, the resistance of the cornea of the treated eye, and hence, the effectiveness of transferring the therapeutic solution for the keratoconus condition, and it is further and substantially increased in case the formulation does not contain NaCl, further demonstrating the importance of the osmolarity of the therapeutic solution to be transferred by the iontophoretic process.

Surprisingly, the lack of dextran and NaCl in the formulations of the compositions according to the present invention is characterizing and innovative, and provides unexpected advantages as compared to the efficacy of the compositions described in the state of the art in the field of ophthalmic solutions administered by iontophoresis and used in treatment of keraroconus.

In particular, the very low osmolarity value, due to the lack of sodium chloride, characterizes the composition showing the best performance in terms of increased resistance of the eye treated with corneal cross-linking following iontophoretic transfer of a solution based on riboflavin.

The solutions according to the present invention may further comprise a buffering system to maintain the pH value in the optimal range between 6.9 and 7.2. A variety of buffering systems are known to the skilled in the art and may be employed in some embodiments according to the present invention. However, in some preferred embodiments of the present invention the sodium phosphate monobasic/dibasic system provides an adequate buffering capacity, such as to maintain the pH in the desired range.

The ophthalmic compositions of the present invention also contain salts of EDTA in the ophthalmologically acceptable form that can be associated, or not associated, to Tris-(hydroxymethyl) aminomethane, also known as tromethamine.

The ophthalmic compositions of the present invention can be prepared in the technical form of collirium and eye drops, gels, and in any case in all pharmaceutical forms that make possible a corneal application followed by iontophoresis according to known techniques; below are examples provided for illustrative purposes, without implying any limitation to the present invention. Other aspects, advantages and modifications within the scope of the invention will be apparent to those skilled in the technical field of the invention.

Pharmaceutical Compositions

The pharmaceutical compositions of the formulations according to the invention are given below, wherein the dosage of the individual components is expressed in percentage by weight.

Example 1

Prep A

| Ingredient | % by weight |
|---|---|
| Riboflavin sodium phosphate | 0.147 |
| Sodium-EDTA | 0.1 |
| Tris-(hydroxymethyl)aminomethane | 0.05 |
| $NaH_2PO_4 \cdot 2H_2O$ | 0.385 |
| $Na_2HPO_4 \cdot 2H_2O$ | 0.217 |
| NaCl | 0.5 |
| $H_2O$ | amount up to 100 ml |
| pH 7 | |
| Osmolarity | 270 mOsm/kg |

Example 2

Prep B

| Ingredient | % by weight |
|---|---|
| Riboflavin sodium phosphate | 0.147 |
| Sodium-EDTA | 0.1 |
| Tris-(hydroxymethyl)aminomethane | 0.05 |
| $NaH_2PO_4 \cdot 2H_2O$ | 0.385 |
| $Na_2HPO_4 \cdot 2H_2O$ | 0.217 |
| $H_2O$ | amount up to 100 ml |
| pH 7 | |
| Osmolarity | 96 mOsm/kg |

EXPERIMENTAL DATA

In order to evaluate the improved ability of transepithelial penetration in rabbit eye of new formulations based on riboflavin delivered by means of iontophoresis compared to those known in the state of the art, the following pilot study was conducted taking in account the effect of the transfer on corneal rigidity.

For the experimental study, which was conducted in compliance with the declarations for the use of animals in ophthalmic and vision research by the European Commission and the Association for Research in Vision and Ophthalmology (ARVO), 12 rabbits, strain GD79b (pigmented), aged 2 and 3 months and weighing between 2.0 and 2.5 kg were used. All animals were identified by an ear tag on arrival and examined prior the test providing particular attention to the condition of the eyes. Before undergoing the experimental procedure all animals were observed for at least three days and used only in the absence of signs of disease.

The twelve pigmented rabbits GD79b strain were randomly divided into four groups of three animals each corresponding to the four types of treatment considered in the study.

Table 1 below summarizes the assignment of the animals in the four treatment groups.

TABLE 1

| Group | Treatment | Animal identification number |
|---|---|---|
| 1 | Application by iontophoresis for 5 minutes and 1 mA of the solution | 11<br>9 |

TABLE 1-continued

| Group | Treatment | Animal identification number |
|---|---|---|
| | described in patent application RM2008A00472 | 4 |
| 2 | Application by iontophoresis for 5 minutes and 1 mA of the PREP A solution | 6 7 3 |
| 3 | Application by iontophoresis for 5 minutes and 1 mA of the PREP B solution | 2 12 5 |
| 4 | Traditional passive application for 30 minutes (0 mA) of the solution described in patent application RM2008A00472 | 10 1 8 |

Group 1 has received corneal administration in the right eye of 0.1% solution described in patent application RM2008A00472 by means of iontophoresis for 5 minutes at the 1 mA current intensity.

Group 2 has received corneal administration in the right eye of 0.1% PREP A solution by iontophoresis for 5 minutes at the 1 mA current intensity.

Group 3 has received corneal administration in the right eye of 0.1% PREP B solution by iontophoresis for 5 minutes at the 1 mA current intensity Group 4 has received corneal administration in the right eye of 0.1% solution described in patent application RM2008A00472 by passive diffusion for 30 minutes.

Iontophoresis Procedure

Animals were subjected to iontophoresis at right eye, while the left eye was used as an untreated control, using an iontophoretic device consisting of two disposable components: an ocular applicator and a return electrode, connected to a reusable generator. The ocular applicator, composed of a polycarbonate reservoir of 10 mm diameter and 4.5 mm height, was filled with the medical foam PUR (Advanced Medical Solutions BV—ref MCF03) and a stainless steel electrode (AISI 304) connected to a generator (cathode) through a cable. The return electrode is an intradermal needle 25G, inserted into the neck of the animal and connected to the generator (anode) through a clip and a cable. The generator delivers a constant current with adjustment range from 0.25 mA to 2.5 mA (10 increments of 0.25 mA for current) and 0.5 min-5 min (10 increments of 0.5 min). During the procedure, the applied voltage is measured with a multimeter.

UV Irradiation

The irradiation by UV-A for the cross-linking of corneal collagen with riboflavin was performed using the medical device VEGA CBM X-Linker constructed by CSO Ophthalmic. The device is equipped with an array of LEDs for emitting light at a wavelength of 370 nm, a diaphragm capable of varying the area to be treated, a system of focus with two intermittent red light LEDs, a micro-camera with the LCD monitor to capture real time images of the procedure, a coaxial fixation light incorporated on the camera that allows the patient to maintain the proper alignment. The power is controlled with a power meter and maintained at 3.0 mW/cm$^2$.

All animals were irradiated totally for 30 minutes, using 6 stages of irradiation each lasting 5 minutes. If necessary, whenever irradiated the cornea becomes dry, one drop of saline was administered. At the end of each irradiation step the cornea was washed with saline solution and one drop of the solution to be administered was added before the beginning of each irradiation step.

After irradiation the animals were sacrificed with an overdose intravenous injection of pentobarbital, both eyes were quickly sampled and used for the biomechanical assay.

The results of the biomechanical assessment of the eyes subjected to the four types of treatment provide an indication of the resistance of the eye following a procedure of cross-linking of the corneal collagen fibers and highlights the differences in the effect produced by the four types of treatment and the three solutions with different composition used.

The data obtained are given in Table 2 below.

TABLE 2

| | | RICROLIN TE with dextran + Iontophoresis | | | | RICROLIN TE PREP A + Iontophoresis | | | | RICROLIN TE PREP B + Iontophoresis | | | | RICROLIN TE with dextran | | | |
|---|---|---|---|---|---|---|---|---|---|---|---|---|---|---|---|---|---|
| | GROUP | 1 | 1 | 1 | | 2 | 2 | 2 | | 3 | 3 | 3 | | 4 | 4 | 4 | |
| | CCT in μm | 700 | 650 | 720 | | 890 | 700 | 720 | | 728 | 700 | 690 | | 730 | 650 | 770 | |
| | strain in % | 14 | 19 | 111 | mean | 13 | 16 | 17 | mean | 112 | 12 | 15 | mean | 18 | 110 | 11 | mean |
| control eye | 0 | 12 | 12 | 12 | 12.0 | 12 | 12 | 12 | 12.0 | 12 | 12 | 12 | 12.0 | 12 | 12 | 12 | 12.0 |
| | 2 | 30 | 34 | 24 | 29.3 | 23 | 31 | 30 | 28.0 | 26 | 24 | 31 | 27.0 | 40 | 34 | 26 | 33.3 |
| | 4 | 53 | 74 | 40 | 55.7 | 43 | 69 | 60 | 57.3 | 51 | 44 | 63 | 52.7 | 78 | 63 | 50 | 63.7 |
| | 6 | 90 | 143 | 70 | 101.0 | 73 | 135 | 106 | 104.7 | 90 | 81 | 113 | 94.7 | 137 | 108 | 93 | 112.7 |
| | 8 | 144 | 255 | 115 | 171.3 | 120 | 238 | 105 | 181.0 | 156 | 137 | 187 | 160.0 | 223 | 176 | 163 | 187.3 |
| | 10 | 222 | 406 | 163 | 270.3 | 192 | 366 | 303 | 287.7 | 248 | 228 | 306 | 260.7 | 345 | 262 | 271 | 292.7 |
| | 12 | 326 | 611 | 277 | 404.7 | 300 | 513 | 469 | 427.3 | 374 | 359 | 470 | 401.0 | 514 | 373 | 422 | 436.3 |
| | 14 | 443 | 841 | 303 | 559.0 | 443 | 692 | 656 | 597.0 | 524 | 535 | 675 | 578.0 | 724 | 493 | 597 | 604.7 |
| | 16 | 554 | 1106 | 615 | 725.7 | 634 | 888 | 842 | 788.0 | 681 | 750 | 894 | 775.0 | 980 | 612 | 786 | 792.7 |
| | 18 | 683 | 1390 | 652 | 908.3 | 843 | 1076 | 1009 | 976.0 | 829 | 1010 | 1130 | 989.7 | 1260 | 716 | 1013 | 996.3 |
| | CCT in μm | 650 | 730 | 700 | 693.3 | 660 | 720 | 750 | 710.0 | 680 | 750 | 680 | 703.3 | 740 | 650 | 650 | 680.0 |
| | strain in % | r4 | r9 | r11 | mean | r3 | r6 | r7 | mean | r12 | r2 | r5 | mean | r8 | r10 | r1 | mean |
| treated eye | 0 | 12 | 12 | 12 | 12.0 | 12 | 12 | 12 | 12.0 | 12 | 12 | 12 | 12.0 | 12 | 12 | 12 | 12.0 |
| | 2 | 24 | 33 | 25 | 27.3 | 27 | 28 | 29 | 28.0 | 41 | 43 | 28 | 37.3 | 32 | 21 | 31 | 28.0 |
| | 4 | 45 | 65 | 44 | 51.3 | 49 | 58 | 62 | 56.3 | 112 | 93 | 60 | 88.3 | 61 | 34 | 80 | 51.7 |
| | 6 | 87 | 126 | 68 | 93.7 | 82 | 103 | 105 | 96.7 | 264 | 176 | 113 | 184.3 | 104 | 56 | 101 | 87.0 |
| | 8 | 147 | 222 | 104 | 157.7 | 133 | 185 | 174 | 164.0 | 537 | 318 | 200 | 351.7 | 161 | 84 | 157 | 134.0 |
| | 10 | 237 | 355 | 156 | 249.0 | 212 | 285 | 266 | 254.3 | 954 | 518 | 338 | 603.3 | 240 | 132 | 232 | 201.3 |
| | 12 | 349 | 516 | 226 | 363.3 | 311 | 435 | 384 | 376.7 | 1494 | 761 | 565 | 940.0 | 337 | 201 | 337 | 291.7 |
| | 14 | 471 | 685 | 321 | 492.3 | 416 | 625 | 526 | 522.3 | 1988 | 1051 | 888 | 1309.0 | 460 | 289 | 471 | 406.7 |

TABLE 2-continued

| GROUP | RICROLIN TE with dextran + Iontophoresis | | | | RICROLIN TE PREP A + Iontophoresis | | | | RICROLIN TE PREP B + Iontophoresis | | | | RICROLIN TE with dextran | | | |
|---|---|---|---|---|---|---|---|---|---|---|---|---|---|---|---|---|
| | 1 | 1 | 1 | | 2 | 2 | 2 | | 3 | 3 | 3 | | 4 | 4 | 4 | |
| 16 | 816 | 869 | 441 | 642.0 | 528 | 805 | 692 | 674.3 | 2326 | 1400 | 1296 | 1674.0 | 597 | 410 | 656 | 554.3 |
| 18 | 775 | 1054 | 565 | 798.0 | 647 | 970 | 869 | 828.7 | 2515 | 1823 | 1739 | 2025.7 | 724 | 562 | 897 | 727.7 |
| Diff r − 1 | 15 | −51 | −28 | 21.3 | 20 | −83 | −37 | −33.3 | 706 | 200 | 32 | 342.7 | −105 | −130 | −39 | −91.3 |

CCT = central corneal thickness
RICROLIN TE = trade name of the solution corresponding to composition described in patent application RM2008A00472.

The data have been represented in a graph shown in FIG. 1, wherein the stress is represented as a function of elongation or tension.

Stress is indicative of the mechanical property of the sample calculated as the ratio between the force applied to a given section of the sample divided by the surface of the section, while the elongation represents the variation of the length undergone by the body divided by its original length.

As shown by the raw data, which are graphically represented in the curve stress vs. tension in FIG. 1, the eyes that have undergone the treatment with the solution of riboflavin corresponding to the PREP B formulation (experimental group 3), containing riboflavin sodium phosphate, EDTA sodium and phosphate buffer and water, iontophoretically delivered, have a central corneal thickness about 3 times greater than the control eyes, and the eyes that have undergone corneal cross-linking receiving, before UV-A irradiation, the solution of riboflavin PREP A (experimental group 2), also containing dextran, or solution comprising both NaCl and dextran, delivered by means of iontophoresis (experimental group 1) or by simple absorption (experimental group 4), as previously described respectively in the patent applications RM2008A00472, PCT/IT2009/000392, PCT/IT2011/000010. The greater central corneal thickness identified in the eyes of the experimental group 3 is the result of a greater effectiveness of the solution PREP B in promoting the cross-linking of corneal collagen fibers able to give greater rigidity to the cornea. In this way the use of the solution PREP B is therapeutically more advantageous in the treatment of keratoconus and other related corneal diseases.

The experimental data relating to the increased resistance of the eye treated by corneal cross-linking, and thus to the increased capacity of penetration and permeation into the cornea of the composition object of the present invention sodium chloride free, the solution PREP B, appears in contrast with what expected on the basis of the concepts of the iontophoretic mechanism: in fact, it is supposed that the presence of sodium chloride in the solution to be transferred by iontophoresis involves an increased conductivity, and a good conductivity of the solution typically results in a good rate of transfer of electric charged masses.

Contrary to what expected, probably the presence of sodium chloride in dissociated form in the composition to be transferred by iontophoresis exerts a competitive effect against the active ingredient (riboflavin phosphate) in saturating the membranes subjected to iontophoresis; alternatively, the presence of dissociated charges of sodium chloride neutralize the charge of riboflavin phosphate, or of other chemical species that act as enhancers in the composition (for example, salts of EDTA in ophthalmologically acceptable form), negatively charged at pH values of experimentation, resulting in a less effective transfer of the active principle promoted by iontophoresis.

Currently applicants of the present patent application are conducting further studies aimed to understand the physic-chemical mechanism at the base of what has been observed.

The invention claimed is:

1. An ophthalmic composition useful for the treatment of keratoconus to be administered by corneal iontophoresis, wherein the cross-linking agent is riboflavin, the pH is between 6.9 and 7.2, and the value of osmolarity is between 90 and 100 mOsm/l, and the following formulation:

| | |
|---|---|
| Riboflavin sodium phosphate | 0.147 g |
| Sodium-EDTA | 0.1 g |
| Tris-(hydroxymethyl)aminomethane | 0.05 g |
| $NaH_2PO_4 \cdot 2H_2O$ | 0.385 g |
| $Na_2HPO_4 \cdot 2H_2O$ | 0.217 g |
| Distilled water | up to 100 g. |

2. The ophthalmic composition according to claim 1, wherein the pH is 7.0, and the osmolarity is 96 mOsm/l.

3. The ophthalmic composition according to claim 2, wherein the pH value equal to 7.0 is obtained through a buffering system comprising sodium phosphate monobasic dihydrate and/or sodium phosphate dibasic dihydrate, in appropriate amounts.

4. The ophthalmic composition according to claim 1, wherein the composition is prepared in a technical form of collirium, eye drops, gels, and in all pharmaceutical forms that enable a corneal application followed by corneal iontophoresis.

5. The ophthalmic composition according to claim 1, wherein the ophthalmic composition is dextran free.

6. The ophthalmic composition according to claim 1, wherein the ophthalmic composition is NaCl free.

7. An ophthalmic composition useful for the treatment of keratoconus to be administered by corneal iontophoresis, wherein the cross-linking agent is riboflavin, the pH is between 6.9 and 7.2, the value of osmolarity is between 90 and 100 mOsm/l, and the composition is NaCl free and the following formulation:
Riboflavin sodium phosphate 0.147 g
Sodium-EDTA 0.1 g
Tris-(hydroxymethyl)aminomethane 0.05 g
$NaH PO_4 \cdot 2H_2O$ 0.385 g
$Na HPO_4 \cdot 2H_2O$ 0.217 g
Distilled water up to 100 g.

8. The ophthalmic composition according to claim 7, wherein the ophthalmic composition is dextran free.

9. The ophthalmic composition according to claim 7, wherein the pH is 7.0, and the osmolarity is 96 mOsm/l.

10. The ophthalmic composition according to claim 7, wherein the pH value equal to 7.0 is obtained through a buffering system comprising sodium phosphate monobasic dihydrate and/or sodium phosphate dibasic dihydrate, in appropriate amounts.

11. The ophthalmic composition according to claim 7, wherein the composition is prepared in a technical form of collirium, eye drops, gels, and in all pharmaceutical forms that enable a corneal application followed by corneal iontophoresis.

* * * * *